United States Patent
Bohlmann et al.

(10) Patent No.: US 6,229,029 B1
(45) Date of Patent: May 8, 2001

(54) 11β-ARYL SUBSTITUTED 14,17-ETHANOESTRATRIENS, METHOD FOR THE PRODUCTION OF THESE COMPOUNDS AND THEIR USE IN THE PRODUCTION OF MEDICAMENTS (75) Inventors: Rolf Bohlmann; Karl Heinrich Fritzemeier; Christa Hegele-Hartung; Rudolf Knauthe; Karsten Parzcyk, all of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/424,913

(22) PCT Filed: Jun. 2, 1998

(86) PCT No.: PCT/EP98/03243

§ 371 Date: Jun. 9, 2000

§ 102(e) Date: Jun. 9, 2000

(87) PCT Pub. No.: WO98/55499

PCT Pub. Date: Dec. 10, 1998

(30) Foreign Application Priority Data

Jun. 2, 1997 (DE) .............................. 197 24 187

(51) Int. Cl.$^7$ .............................. C07D 245/00; C07J 53/00
(52) U.S. Cl. .............................................. 552/510; 540/470
(58) Field of Search ............................... 540/470; 552/510

(56) References Cited

FOREIGN PATENT DOCUMENTS 0 384 842 A1   8/1990   (EP) .
WO 93/13123   7/1993   (WO) .

*Primary Examiner*—Barbara P. Badio
(74) *Attorney, Agent, or Firm*—Millen White Zelano & Branigan

(57) ABSTRACT

This invention describes 11β-aryl-substituted 14,17-ethanoestratrienes of general formula (I). The new compounds are selective estrogens whose action occurs in a tissue-selective manner. The estrogenic action occurs in particular on bone, in the cardiovascular system and in the CNS (central nervous system). Only a slight estrogenic action or no estrogenic action occurs in the uterus and in the liver, however. The compounds are suitable for the production of pharmaceutical agents for use in numerous indications (for example for hormone replacement therapy, prevention and treatment of osteoporosis).

16 Claims, 7 Drawing Sheets

Figure 1

Stimulation of the Luminal Uterus Epithelium in Immature Rats

[Key:]

Stimulierung des luminalen Uterusepithels in % von E2 =
    Stimulation of the luminal uterus epithelium in % of E2

Dosis in mg/kg Körpergewicht = Dose in mg/kg of body weight

Verbindung V/B = Compound V/B

Figure 2

Trabecular Bone Density of the Distal Femur

7 mm Away from the Ball of the Joint

Compound A

[Key:]

Knochendichte in mg Ca/ccm = Bone density in mg of Ca/ccm

Vehikel = vehicle 0,3 µg 17β-Estradiol = 0.3 µg of 17β-estradiol

Verb. A = compound A

Figure 3

Uterus Weight (relative)

Compound A

[Key:]

mg/100g KG = mg/100 g of body weight

Kontr. sham = sham control 0,3 μg 17β-Estradiol = 0.3 μg of 17β-estradiol

Verb. A = compound A

Figure 4

Trabecular Bone Density of the Proximal Tibia

5 mm Away from the Ball of the Joint

Compound A

[Key:]

Knochendichte in mg Ca/ccm = Bone density in mg of Ca/ccm 0,3 µg 17ß-Estradiol = 0.3 µg of 17ß-estradiol Verb. A = compound A

Figure 5

Uterus Weight (relative)

Compound A

[Key:]

mg/100g KG = mg/100 g of body weight

Kontr. ovx = ovx control 0,3 µg 17β-Estradiol = 0.3 µg of 17β-estradiol

Verb. A = compound A

Figure 6

Trabecular Bone Density of the Proximal Tibia 5 mm Away from the Ball of the Joint Compound V

[Key:]

Knochendichte in mg Ca/ccm = Bone density in mg of Ca/ccm 0,3 µg 17ß-Estradiol = 0.3 µg of 17ß-estradiol Verb. V = compound V

Figure 7

Dissociation of Bone Action/Uterus Action

[Key:]

% Wirkung von 17β-Estradiol = % of action of 17β-estradiol

Verbindung = compound

Versuch 1/2 Knochenwirkung = test 1/2 of the bone action

Uterusepithel = uterus epithelium

Dosis in mg/kg = dose in mg/kg

11β-ARYL SUBSTITUTED 14,17-ETHANOESTRATRIENS, METHOD FOR THE PRODUCTION OF THESE COMPOUNDS AND THEIR USE IN THE PRODUCTION OF MEDICAMENTS

This application is a 371 of PCT/EP98/03243 filed Jun. 2, 1998.

This invention relates to 11β-aryl-substituted 14,17-ethanoestratrienes of general formula I (I)

in which
R$^1$ stands for a hydrogen atom, a C$_1$–C$_{12}$ alkanoyl group, a benzoyl group, a straight-chain or branched-chain C$_1$–C$_{12}$ alkyl group, a C$_3$–C$_7$ cycloalkyl group or a C$_4$–C$_8$ alkylcycloalkyl group, which all can optionally be substituted, R$^2$ stands for a hydrogen atom or an optionally substituted C$_1$–C$_{12}$ alkanoyl group and R$^3$ stands for a grouping —(CH$_2$)$_n$NR$^4$R$^5$ or —(CH$_2$)$_n$OCH$_2$CONR$^4$R$^5$ or —(CH$_2$)$_n$S(O)$_m$R$^6$, in which
n is 4, 5, 6 or 7,
m is 0, 1 or 2, R$^4$ or R$^5$, independently of one another, mean a hydrogen atom or a straight-chain or branched, optionally substituted C$_1$–C$_8$ alkyl group, which can also be partially or completely fluorinated, or R$^4$ and R$^5$ together mean a methylene to pentamethylene group —(CH$_2$)$_p$— (p=1–5), and R$^6$ has the meaning of R$^4$ or R$^5$ or is an optionally substituted aryl or arylalkyl radical, whereby the alkyl radical can have up to 6 carbon atoms in it and the aryl radical alone or in the arylalkyl radical is a 5- or 6-membered monocyclic ring or a condensed 8- to 10-membered ring system, and the aryl radical can have one or more heteroatoms that are selected from among oxygen, nitrogen and sulfur.

Alkyl groups that are mentioned within the scope of this invention as R$^4$ and R$^5$ are, for example, the methyl, ethyl, n- or iso-propyl, n-, iso- or tert-butyl, pentyl, neo-pentyl, hexyl, heptyl or octyl group.

In the C$_1$–C$_{12}$ alkyl group R$^1$ the higher homologues such as, for example, the nonyl to dodecyl group, are added.

As a C$_3$–C$_7$ cycloalkyl group, for example, the cyclopropyl, cyclopentyl, cyclohexyl and cycloheptyl radical can be mentioned.

Typical representatives of a C$_4$–C$_8$ alkylcycloalkyl group are the methylcyclopropyl radical, the methylcyclopentyl radical and the methylcyclohexyl radical.

A C$_1$–C$_{12}$ alkanoyl radical, which can stand for R$^1$ and/or R$^2$, is defined as the acyl radicals of the straight-chain and branched C$_1$–C$_{12}$ alkanecarboxylic acids, thus, for example, the formyl, acetyl, propionyl, butyryl or isobutyl radical, as well as the higher homologues of the radicals mentioned above.

As a partially or completely fluorinated straight-chain or branched C$_1$–C$_8$ alkyl group, for example, the trifluoromethyl group, 2,2,2-trifluoroethyl group, 4,4,4-trifluorobutyl group, 3,3,4,4,4-pentafluorobutyl group, 4,4,5,5,5-pentafluoropentyl group or the nonafluorobutyl group is to be mentioned.

The following radicals can represent aryl radical R$^6$ or the aryl radical within arylalkyl radical R$^6$:

a monocyclic, carbocyclic radical, for example the phenyl radical;

a monocyclic, heterocyclic radical, for example the thienyl, furyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, tetrazolyl radical, namely all possible isomers relative to the positions of the heteroatoms as. well as the interface site to the sulfur atom in the side chain;

a condensed, carbocyclic radical, for example the naphthyl or phenanthrenyl radical, a condensed radical, which consists of carbocyclic and heterocyclic radicals, for example, the benzofuranyl, benzothienyl, benzimidazolyl, benzothiazolyl, naphtho[2,3-b]thienyl, thianthrenyl, isobenzofuranyl, chromenyl, xanthenyl, phenoathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, acridinyl, phenazinyl, phenothiazinyl, phenoxazinyl, indolinyl, isoindolinyl, imidazopyridyl, imidazopyrimidinyl or a condensed polyheterocyclic system, for example furo[2,3-b]pyrrole or thieno[2,3-b]furan.

As substituents to radicals R$^1$, R$^2$, R$^4$, R$^5$ and R$^6$, the substituents below are considered, whereby the radicals can be substituted with these substituents the same or different in one or more places:

Halogen atoms: fluorine, chlorine, bromine, iodine;

Amino, alkylamino or dialkylamino groups, in which the alkyl radical has 1 to 4 carbon atoms; especially methylamino or ethylamino, dimethylamino, diethylamino or methylethylamino;

Hydroxyl groups;

Carboxyl groups that are present in free form, esterified form or in the form of a salt; esterified with a carboxycarbonyl group, for example methoxycarbonyl or ethoxycarbonyl; as a salt for example in the form of the sodium or potassium salt;

Alkyl groups with 1 to 8 carbon atoms, such as, for example, the methyl, ethyl, n- or iso-propyl, n-, iso- or tert-butyl group, optionally substituted with one or more halogen atoms, for example with fluorine such as the trifluoromethyl group;

Oxo, cyano, nitro or formyl groups;

Acyl groups such as acetyl, propionyl, butyryl, benzoyl;

Acyloxy groups such as acetoxy, radicals of formula —O—CO—(CH$_2$)$_n$—COOH with n=1 to 5;

Alkoxy groups, such as, for example, methoxy, ethoxy, propoxy, isopropoxy, butoxy;

Alkylthio groups, for example, methylthio, ethylthio, propylthio, isopropylthio, butylthio;

Carbamoyl groups;

Alkenyl groups, for example vinyl, propenyl;

Alkinyl groups, for example ethinyl, propinyl;

Aryl groups, such as phenyl, furyl, thienyl.

$R^1$ and $R^2$ respectively stand preferably for a hydrogen atom.

If $R^1$ and/or $R^2$ is to be an alkyl group, a methyl or ethyl group is preferred.

If $R^1$ and/or $R^2$ stands for an alkanoyl group, primarily an acetyl or propionyl group is meant. A benzoyl group is also part of the preferred representatives of these substituents.

As a cycloalkyl group for substituents $R^1$ and $R^2$, mainly the cyclopropyl and cyclopentyl groups are to be mentioned, and as an alkycycloalkyl group, the methylcyclopropyl and methylcyclopentyl groups are to be mentioned.

Within the groupings that stand for $R^3$, the substituents hydrogen, methyl, ethyl, propyl, butyl, 4,4,5,5,5-pentafluoropentyl and mainly the substituent combinations of 2 hydrogen atoms, n-butyl/methyl, —$(CH_2)_4$—, and —$(CH_2)_5$— are preferred for $R^4$ and $R^5$.

$R^6$ preferably stands for an n-pentyl, 4,4,5,5,5-pentafluoropentyl or —$CH_2$-2, 3- or 4-pyridine group.

In particular, $R^3$ stands for one of the following substituents:

—$(CH_2)_5S(CH_2)_4CH_3$
—$(CH_2)_5SO(CH_2)_4CH_3$
—$(CH_2)_5SO_2(CH_2)_4CH_3$
—$(CH_2)_5SO(CH_2)_3CF_2CF_3$
—$(CH_2)_5SO_2$—$CH_2$-(2-pyridyl)
—$(CH_2)_5SO_2$—$CH_2$-(3-pyridyl)
—$(CH_2)_5SO_2$—$CH_2$-(4-pyridyl)
—$(CH_2)_6$—O—$CH_2C(O)N(CH_3)C_4H_9$
—$(CH_2)_5SO_2(CH_2)_3CF_2CF_3$
—$(CH_2)_5SO$—$CH_2$-(2-pyridyl)
—$(CH_2)_5SO$—$CH_2$-(3-pyridyl)
—$(CH_2)_5SO$—$CH_2$-(4-pyridyl)
—$(CH_2)_5$-pyrrolidinyl
—$(CH_2)_6S(CH_2)_3CF_2CF_3$
—$(CH_2)_6SO(CH_2)_3CF_2CF_3$
—$(CH_2)_6SO(CH_2)_3CF_2CF_3$
—$(CH_2)_6SO_2(CH_2)_3CF_2CF_3$ For the purposes of the invention, especially preferred compounds are:

14α,17α-Ethano-11β-{4-[5-(pyrrolidin-1-yl)pentyloxy]phenyl}-1,3,5(10)-estratriene-3,17β-diol 14α,17α-ethano-11β-{4-[5-(pentylthio)pentyloxy]phenyl}-1,3,5(10)-estratriene-3,17β-diol 14α,17α-ethano-11β-{4-[5-(pentanesulfinyl)pentyloxy]phenyl}-1,3,5(10)-estratriene-3,17β-diol 14α,17α-ethano-11β-{4-[5-(pentanesulfonyl)pentyloxy]-phenyl}-1,3,5(10)-estratriene-3,17β-diol 14α,17α-ethano-11β-{4-[5-(4,4,5,5,5-pentafluoropentylsulfinyl)pentyloxy]phenyl}-1,3,5(10)-estratriene-3,17β-diol 14α,17α-ethano-11β-{4-[5-(2-pyridinomethylsulfonyl)pentyloxy]phenyl}-1,3,5(10)-estratriene-3,17β-diol 14α,17α-ethano-11β-{4-[6-(4,4,5,5,5-pentafluoropentylthio)hexyloxy]-phenyl}-1,3,5(10)-estratriene-3,17β-diol 14α,17α-ethano-11β-{4-[6-(4,4,5,5,5-pentafluoropentyl)sulfinyl]hexyloxy}phenyl-1,3,5(10)-estratriene-3,17β-diol 14α,17α-ethano-11β-{4-[6-(4,4,5,5,5-pentafluoropentyl)sulfonyl]hexyloxy}phenyl-1,3,5(10)-estratriene-3,17β-diol 14α,17α-ethano-11β-{4-[5-(2-pyridinomethylsulfinyl)pentyloxy]phenyl}-1,3,5(10)-estratriene-3,17β-diol 14α,17α-ethano-11β-{4-[5-(4,4,5,5,5-pentafluoropentyl)sulfonyl]pentyloxy}phenyl-1,3,5(10)-estratriene-3,17β-diol 2-(6-(4-[10-{14,17-ethano-3,17-dihydroxyestra-1,3,5(10)-trien-11β-yl}]-phenoxy)-hexyloxy)acetic acid-(N-butyl-N-methyl)-amide The 19-Nor steroids with an 11β-side chain of formula —X—Y—S(O)$_m$—Z that are described in WO-A 93/13123 and the 19-Nor steroids with an 11β-side chain of formula —X—Y—Z—C(O)—N(RA)(RA') that are described in EP-A 0 384 842 can be considered as the compounds that come closest to the new compounds of general formula I. In this connection, X, Y, Z, RA, and RA' can be selected so that these side chains are identical to the 11β-substituents according to this invention, in which $R^3$ means the grouping —$(CH_2)_nOCH_2CONR^4R^5$ or —$(CH_2)_nS(O)_mR^6$.

The compounds of the prior art, however, do not have the 14α,17α-ethano bridge that is present in the compounds according to the invention. The known compounds can be, i.a., compounds with estrogenic or antiestrogenic properties. In this case, the compounds can be free of uterotrophic action.

In contrast, 14α,17α-ethanoestratrienes that in 11β-position have a nonyl radical that is substituted terminally with an amide, amine or sulfinyl group are described in WO 93/06124. These compounds are described exclusively as compounds with an especially high affinity to the estrogen receptor, which, even after peroral administration, are pure antiestrogens with strong antiestrogenic action. These compounds are distinguished from the previous ones by the substitution feature in 11β-position of the steroid skeleton.

The compounds according to the invention are selective estrogens, whose action occurs in a tissue-selective manner. The estrogenic action occurs in particular on bone, in the cardiovascular system and in the CNS (central nervous system). Only a slight estrogenic action or no estrogenic action occurs in the uterus and in the liver, however. The compounds can also have antiestrogenic activity, which can be detected in, for example, an anti-uterus growth test or in tumor models.

Compounds with such a profile have recently been referred to as Selective Estrogen Receptor Modulators (SERMs) (Structure-Activity Relationships of Selective Estrogen Receptor Modulators: Modifications to the 2-Arylbenzothiophene Core of Raloxifene, T. A. Grese et al., J. Med. Chem. 1997, 40, 146–167). The most prominent representative of this compound class is raloxifene, which is currently under clinical evaluation for the prevention and the treatment of postmenopausal osteoporosis.

Pharmacological Study of the Compounds According to the Invention Antiestrogenic/Estrogenic Action In Vitro The antiestrogenic action of the compounds according to the invention was determined in transactivation assays [Demirpence, E.; Duchesne, M.-J.; Badia, E.; Gagne, D.; and Pons, M.: MVLN Cells: A Bioluminescent MCF-7-Derived Cell Line to Study the Modulation of Estrogenic Activity; J. Steroid. Molec. Biol. Vol. 46, No. 3, 355–364 (1993) as well as Berry, M.; Metzger, D.; Chambon, P.: Role of the Two Activating Domains of the Estrogen Receptor in the Cell-Type and Promoter-Context-Dependent Agonistic Activity of the Anti-estrogen 4-Hydroxytamoxifen; The EMBO Journal Vol. 9, 2811–2818 (1990)]. The transactivation tests were carried out in HeLa or MVLN cells.

The HeLa cells are transiently transfixed with human estrogen receptor-expression vector (HEGO) and vit-TK-CAT reporter genes, and the MVLN cells are transfixed in a stable manner with the reporter gene Vit-TK-LUC. The antiestrogenic active strength in the presence of 0.1 nM of estradiol was determined.

The partial estrogenic action was also determined by transactivation assays. HeLa cells were transfixed with estrogen receptors and a reporter gene, which consists of the estrogen-response element of the progesterone receptor and the CAT-gene. The test was performed as described: Savouret et al., EMBO J. 10, 1875–1883 (1991).

Table 1 below indicates the results for the compounds according to the invention 14α,17α-ethano-11β-{4-[5-(2-pyridinomethylsulfonyl)pentyloxy]phenyl}-1,3,5(10)-estratriene-3,17β-diol (compound A) and 14α,17α-ethano-11β-{4-[5-(2-(pyridinomethylsulfinyl)pentyloxy]phenyl}-1,3,5(10)-estratriene-3,17β-diol (compound B) and for 11β-{4-[5-(2-pyridinomethylsulfinyl)pentyloxy]phenyl}-1,3,5(10)-estratriene-3,17β-diol (compound V) according to WO 93/13123. Compound V from the prior art is distinguished from compound B only by the absence of the 14α,17α-ethano bridge.

The influence of the compounds according to the invention on the uterus was examined in the uterus growth test (estrogenic action) and in the anti-uterus growth test (antiestrogenic action), both performed on infant rats.

Estrogenic/Antiestrogenic Action In Vivo Uterus Growth Test on Infant Rats (n=5 Animals/Group)

In infant animals, both uterus and vagina show one of the estrogenic activity-dependent weight increases in their treatment with an estrogenically active substance. In the uterus, under estrogenic action, moreover, it results in a proliferation and height increase of the luminal epithelium.

Immature, normal rats (body weight 40–50 g) receive the substance s.c. over 3 days (d1–d3). On day 4 (d4), the animals are sacrificed with $CO_2$. The uteri are prepared outside and weighed. A piece of the uterus, preferably a uterine horn, is set in formaldehyde for the histological evaluation and embedded in paraffin. The stimulation of the organ weights (relative to mg/100 g of body weight) and the epithelial height are indicated in percentage stimulation in comparison to the reference compound 17β-estradiol. (Substitution dose $E_2$ 0.3 μg/animal).

Table 2 below indicates the results for the compounds according to the invention 14α,17α-ethano-11β-{4-[5-(2-pyridinomethylsulfonyl)pentyl-oxy]phenyl}-1,3,5(10)-estratriene-3,17β-diol (compound A) and 14α,17α-ethano-11β-{4-[5-(2-pyridinomethylsulfinyl)pentyl-oxy]phenyl}-1,3,5(10)-estratriene-3,17β-diol (compound B) and for 11β-{4-[5-(2-pyridinomethylsulfinyl)pentyloxy]phenyl}-1,3,5(10)-estratriene-3,17β-diol (compound V) according to WO 93/13123. Compound V from the prior art is distinguished from compound B only by the absence of the 14α,17α-ethano bridge.

After s.c. administration, compound A represents a compound without any estrogenic action in the uterus.

Figure 1:
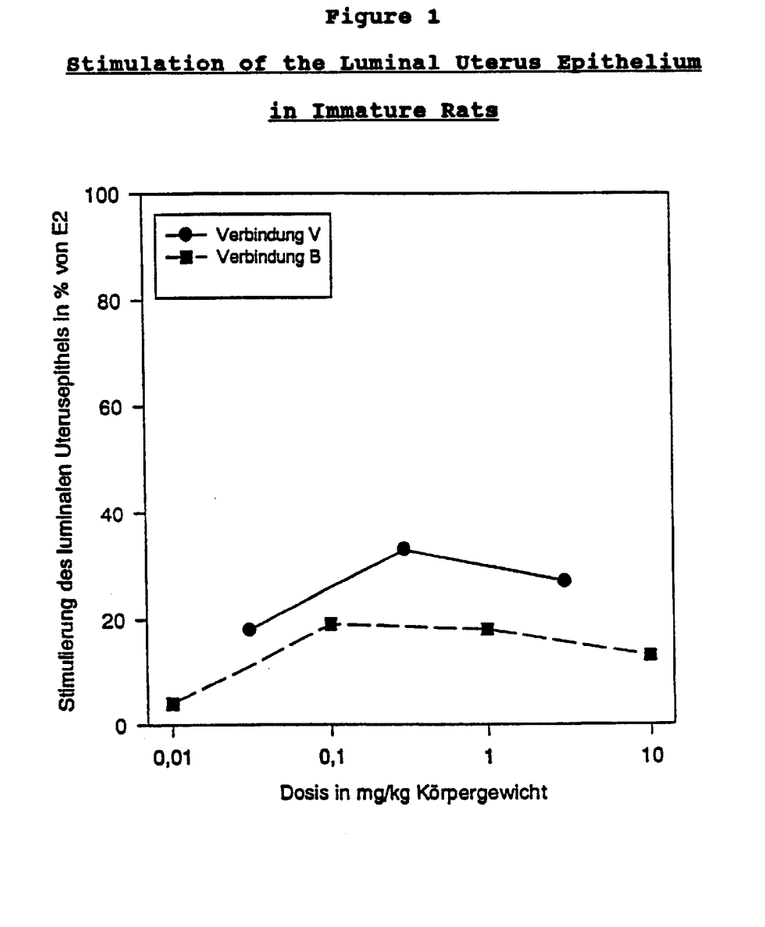
FIG. 1 is a comparative graph of two compounds showing their stimulation of the luminal uterus epithelium in immature rats.

Compounds B and V are both represented in the uterus growth test as compounds with low estrogenic action, whereby compound B in the considered dose range is approximately half as strongly estrogenically active as the analogous compound V without the $C_2$-bridge. These ratios are presented in Table 2 and FIG. 1.

Anti-Uterus Growth Test in Infant Rats (n=5 Animals/Group)

The uterus of infant estrogen-substituted rats can be used as a test model to detect a direct action of substances with antiestrogenic properties. The parameter of the estrogenic action is the uterus growth that is induced by estradiol in infant rats and that is inhibited by simultaneous administration of a substance with antiestrogenic action.

The test substances are treated s.c. on 3 successive days (d1–d3) in combination with a substitution dose of 0.3 μg/animal/day of 17β-estradiol. As a positive control, 17β-estradiol alone is used; the vehicle group is used as a negative control. On day 4 (d4), the animals are sacrificed, uteri and vaginae are prepared outside and weighed. The organ weights are converted into mg/100 g of body weight, and then the mean and the standard deviation for each dosage are calculated. The inhibition of the uterus or vaginal growth that is induced by 17β-estradiol is indicated in % as inhibition.

Table 3 below indicates the results for the compounds according to the invention 14α,17α-ethano-11β-{4-[5-(2-pyridinomethylsulfonyl)-pentyloxy]phenyl}-1,3,5(10)-estratriene-3,17β-diol (compound A) and 14α,17α-ethano-11β-{4-[5-(2-pyridinomethylsulfinyl)pentyloxy]-phenyl}-1,3,5(10)-estratriene-3,17β-diol (compound B) and for 11β-{4-[5-(2-pyridinomethylsulfinyl)pentyloxy]phenyl}-1,3,5(10)-estratriene-3,17β-diol (compound V) according to WO 93/13123. Compound V from the prior art is distinguished from compound B only by the absence of the 14α,17α-ethano bridge.

All three tested compounds are accordingly strongly antiestrogenically active in the uterus.

With respect to their action on the uterus, the compounds according to the invention are thus superior to the compounds of the prior art within the meaning of this invention to the extent that they have little or even no estrogenic action in this organ.

Bone Studies

Methods 3-month-old female rats are ovariectomized and treated once daily with the test compound immediately after the operation for 28 days. The administration is done subcutaneously in castor oil/benzyl benzoate or arachis oil/ethanol. The animals are sacrificed on the day after the last administration, and femurs, tibiae and uteri are removed. The uteri are weighed, fixed and worked up for histological studies. The determination of the bone density is carried out ex vivo on prepared long bones with use of pQCT (Quantitative Computer Tomography). The measurements are performed at a distance of 5–7 mm from the ball of the joint on the distal femur or the proximal tibia.

As an alternative, the action on the bone is determined by measuring the trabecular bone surface area of the secondary spongiosa in histological preparations of the distal femur or the proximal tibia. The result is expressed as the proportion, in percent, of the trabecular bone surface area in the measured total bone surface area (TB/BV). The bone density that is measured with use of QCT and the trabecular bone surface area that is determined in the histological section correlate well to one another. A comparison of the two measurement variables is therefore permissible.

Figure 2:
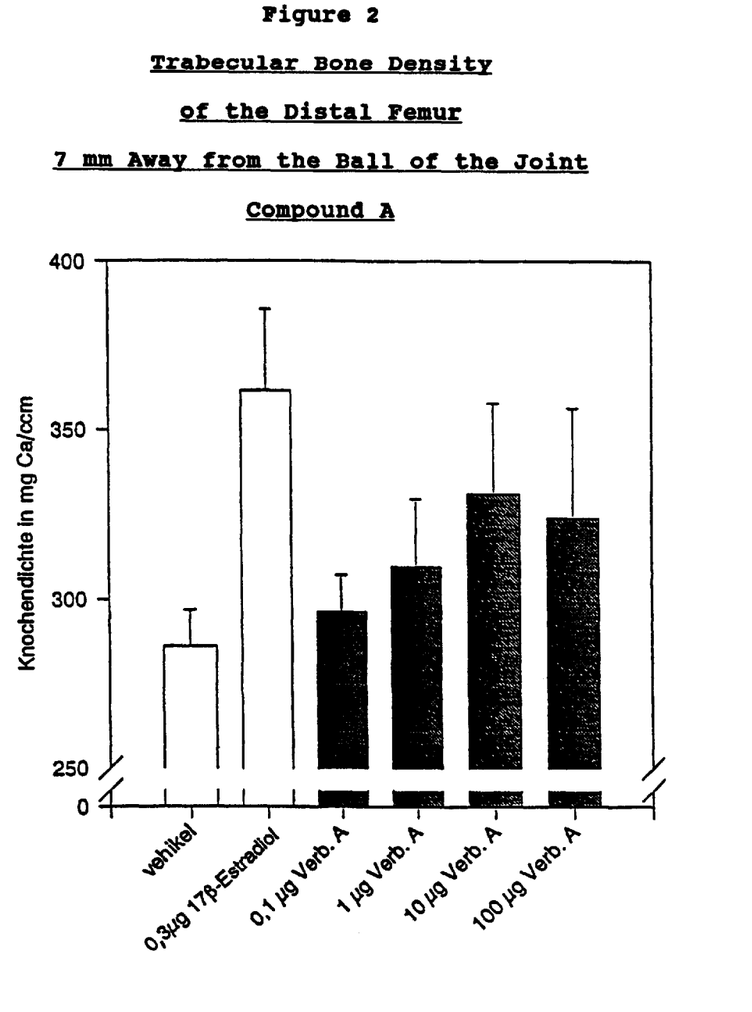
FIG. 2 is a bar graph showing the relative trabecular bone density of the distal femur 7 mm away form the ball of the joint for rats treated with a control, with an estradiol and with varying amounts of compound A.
Figure 3:
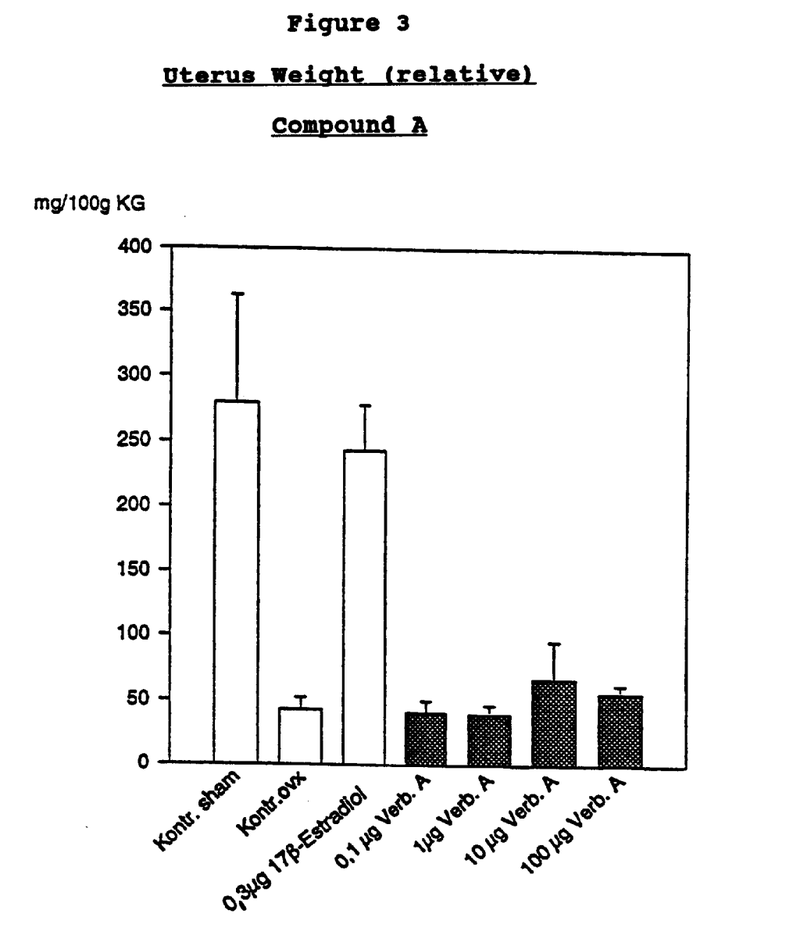
FIG. 3 bar graph showing the relative uterus weight for rats treated with a sham control, with an estradiol and with varying amounts of compound A.

About 50% of the bone density of the animals is lost by the ovariectomy. The degradation of the bone density is prevented or inhibited by the treatment with a compound of general formula I according to this invention (compound A). In Table 4 and FIG. 2, the results of this test for doses of 0.1–100 μg/animal/day are presented. The bone density was measured on the distal femur; for comparison, the trabecular bone surface area in the proximal tibia was measured. The data that are contained in Table 4 mean specifically:

sham: sham-operated animals; these animals are not ovariectomized, they were only cut to produce the operation effect for the control group ovx: ovariectomized group BMD-qCT bone mineral density, determined by quantitative computer tomography; using this process, the calcium density is measured in one section through the bone as an indicator of the bone density TB/TV trabecular bone surface area/total bone surface area; histologically determined In the dose range between 10 and 100 µg, compound A has a protective action of 50–60% in comparison to 17β-estradiol. As FIG. 3 indicates, compound A, in contrast to 17β-estradiol, stimulates the uterus weight, but at most does so marginally.

Figure 4:
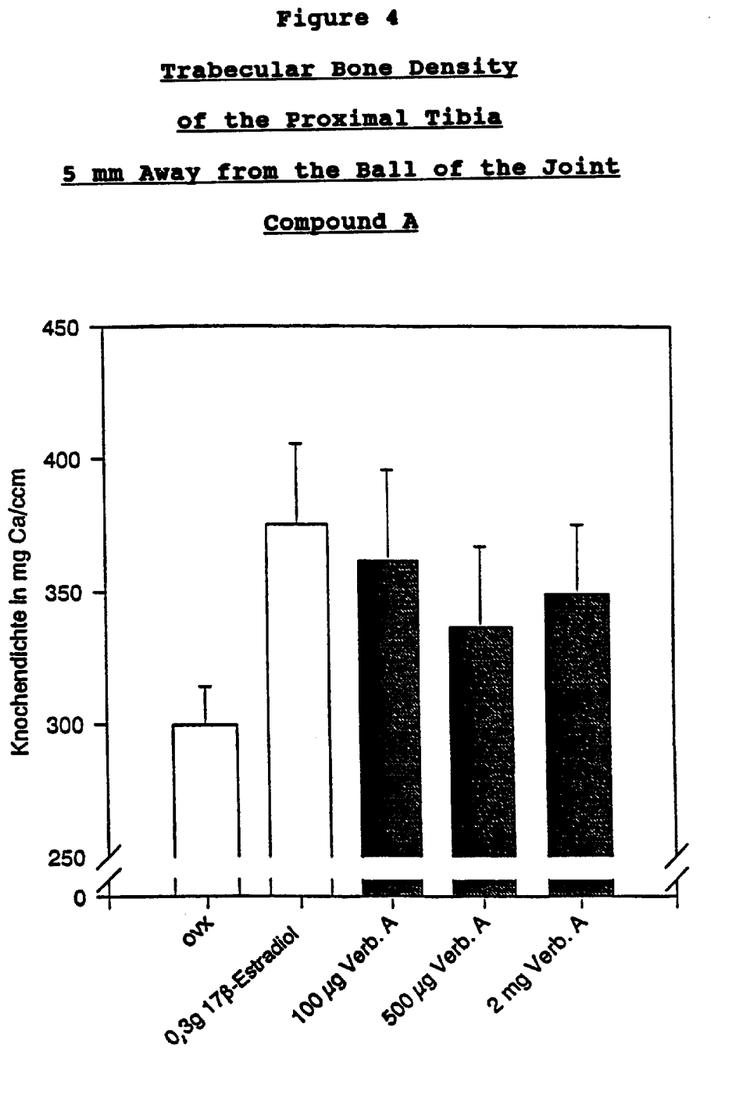
FIG. 4 is a bar graph showing the relative trabecular bone density of the proximal tibia 5 mm away form the ball of the joint for rats treated with a control, with an estradiol and with varying amounts of compound A.

In another test, the bone-protecting action of compound A was also determined in dosages of 100–2000 µg/animal/day. In this case, the bone density was measured in the proximal tibia. The results are shown in Table 5 and in FIG. 4. The meaning of the abbreviations is as already indicated in Table 4.

Figure 5:
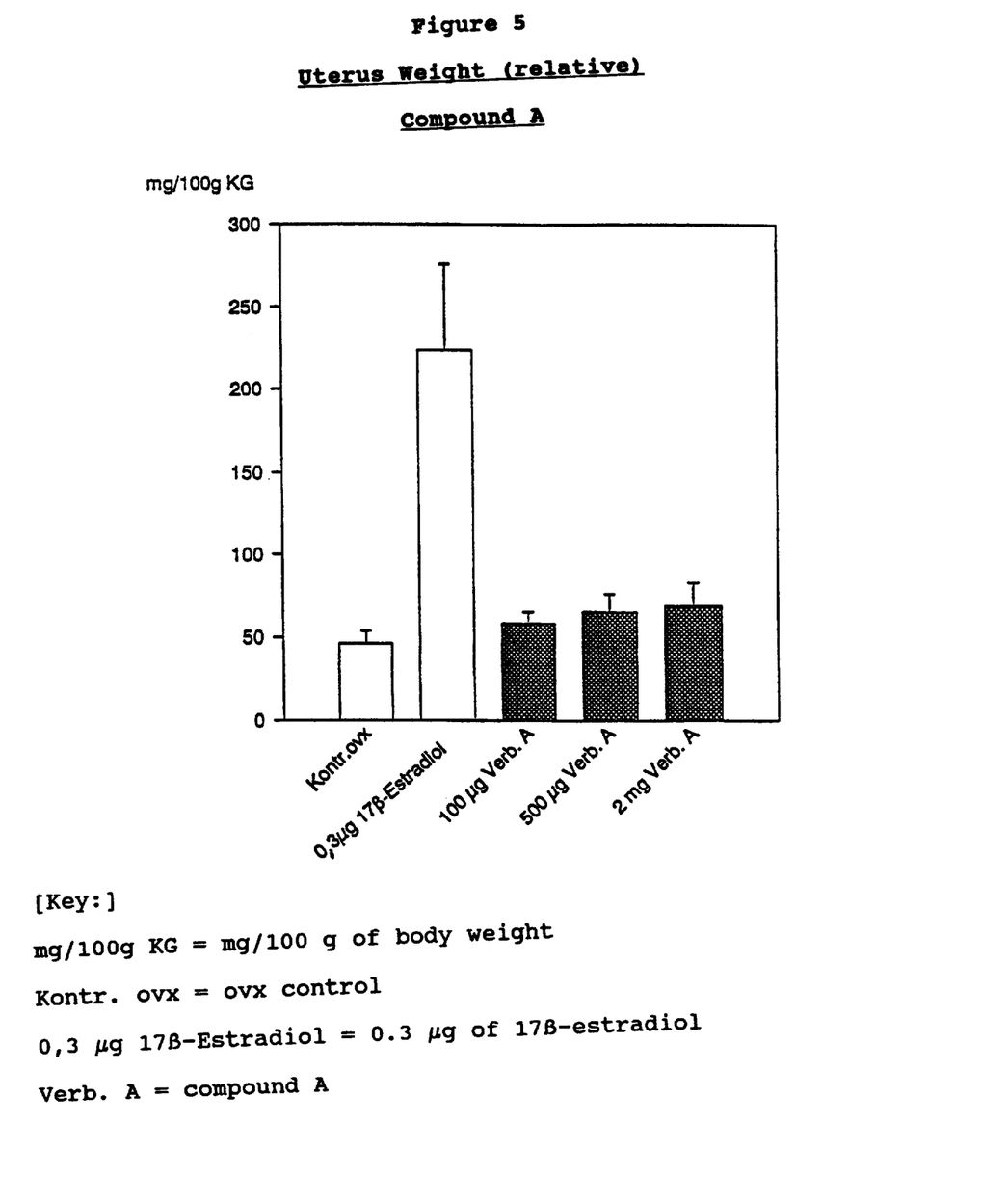
FIG. 5 is a bar graph showing the relative uterus weight for rats treated with an ovx control, with an estradiol and with varying amounts of compound A.

At a dose of 100 µg/animal/day, compound A has an action of about 80% in comparison to 17β-estradiol. This action can no longer be increased by increasing the dose. As FIG. 5 indicates, compound A also in this test stimulates the uterus weight only marginally in all tested dosages.

For compound B according to the invention, their bone-protecting action was also determined (Table 6). For this purpose, the parameter of TB/TV was determined, which, however, with respect to the informational value for the bone-protecting activity correlates well to the parameter of BMD-qCT that is determined for compounds A and V. This can be ascertained from Table 4; both parameters were determined for compound A.

In the case of a weakened or absent uterotrophic estrogenic action, the compounds according to the invention simultaneously have an action that is similar to or even better than the closest compounds of the prior art with respect to their bone-protecting action. In the case of comparable or better bone action, the compounds according to the invention stimulate the uterus less or not at all in contrast to the known compounds.

Figure 6:
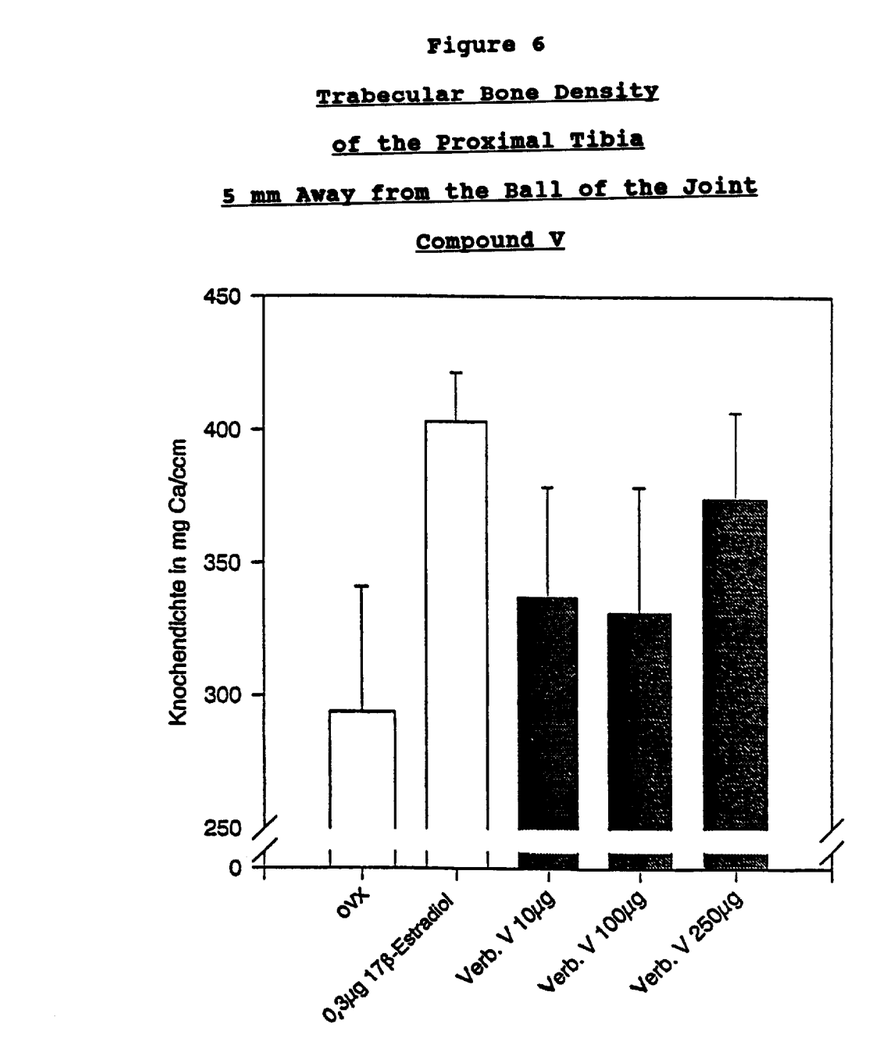
FIG. 6 is a bar graph showing the relative trabecular bone density of the proximal tibia 5 mm away form the ball of the joint for rats treated with a control, with an estradiol and with varying amounts of compound V.

The compounds according to the invention are thus considerably more dissociated than the closest compounds of the prior art within the meaning of a selective action on bone or at least with respect to a weakened action on the uterus. This shows the comparison, indicated in Table 7 and FIG. 6, with compound V of the prior art. With 100 µg/animal/day, compound A has an action of about 80% of 17β-estradiol on the trabecular bone of the proximal tibia. This action is achieved only with 250 µg/animal/day of comparison compound V. Compound A according to the invention is thus more potent than comparison compound V by a factor of 3 with respect to the bone-protecting action.

Figure 7:
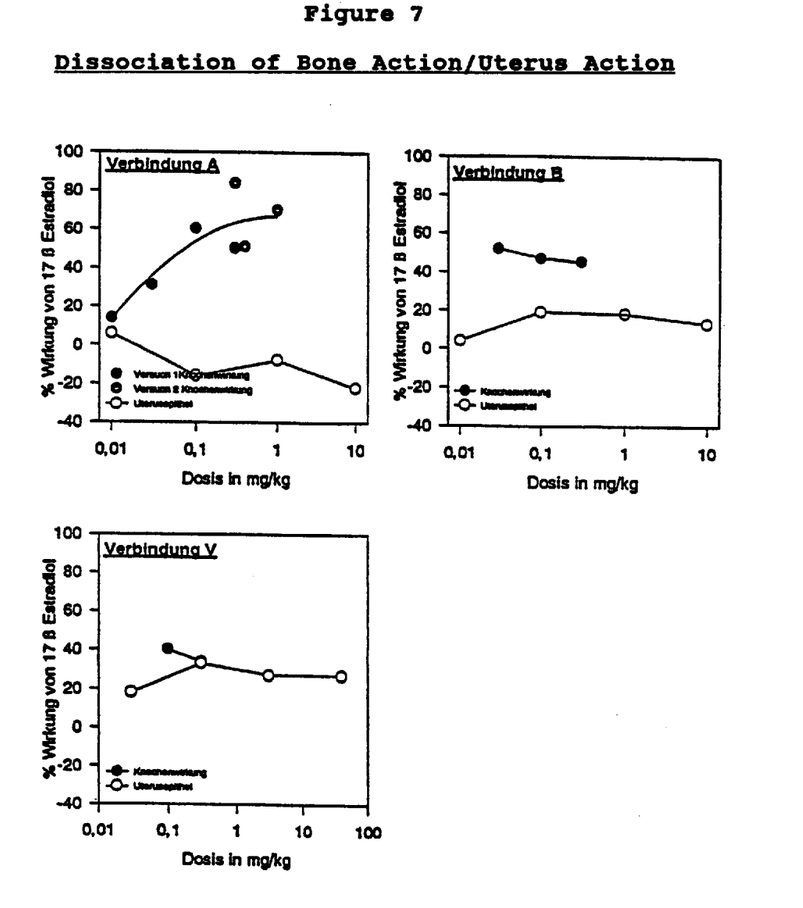
FIG. 7 provides three graphs showing the dissociation of bone action/uterus action for three compounds.

The ratios that are described above are all summarized in FIG. 7. There, for compounds A, B and V, their bone-protecting actions are compared to the action of estrogen on the uterus (parameter: uterus epithelial height) as a function of dosage, in each case relative to the action of 17β-estradiol. Compound A is the most dissociated, compound B is also considerably dissociated, while the two curves coincide for compound V.

Both after oral and parenteral administration, the compounds can be used for the following indications:

Alleviation of the symptoms of male menopause and female menopause, i.e., for male and female hormone replacement therapy (HRT), specifically both for prevention and for treatment; for treatment of symptoms that accompany a dysmenorrhea; treatment of dysfunctional uterine bleeding; treatment of acne; prevention and treatment of cardiovascular diseases; treatment of hypercholesteremia and hyperlipidemia; prevention and treatment of arteriosclerosis; for inhibition of the proliferation of arterial smooth muscle cells; for treatment of the respiratory distress syndrome in newborns; treatment of primary pulmonary high blood pressure; for prevention and treatment of osteoporosis; for prevention of bone loss in postmenopausal women, in women who have hysterectomies or in women who were treated with LHRH agonists or antagonists; inhibition of sperm maturation; treatment of rheumatoid arthritis; for prevention of Alzheimer's disease; treatment of endometriosis; treatment of myomas; treatment of myomas and endometriosis in combination with LHRH analogs; treatment of hormone-dependent tumors; e.g., of breast cancer, treatment of prostatic diseases.

In addition, the compounds according to the invention are suitable based on their pharmacological profile both for male and for female contraception.

The compounds can also be used in combination with the natural vitamin D3 or with calcitriol analogs for the formation of bone or as supporting therapies to therapies that cause a loss in bone mass (for example a therapy with glucocorticoids, chemotherapy).

Finally, the compounds of general formula I are used in connection with progesterone receptor-antagonists or in connection with pure estrogens, specifically especially for use in hormone replacement therapy and for treatment of gynecological disorders and for female birth control. A therapeutic product that contains an estrogen and a pure antiestrogen for simultaneous, sequential or separate use for the selective estrogen therapy of perimenopausal or postmenopausal conditions is already described in EP-A 0 346 014.

The amount that is to be administered of a compound of general formula I fluctuates within a wide range and can cover any effective amount. Based on the condition to be treated and the type of administration, the amount of the administered compound can be 0.01–10 mg/kg of body weight, preferably 0.1–5 mg/kg of body weight each day.

In humans, this corresponds to a dose of 0.8 to 800 mg, preferably 8 to 400 mg, daily.

According to the invention, a dosage unit contains 0.4 to 400 mg of one or more compounds of general formula I.

The compounds according to the invention are suitable for the production of pharmaceutical compositions and preparations. As active ingredients, the pharmaceutical compositions or pharmaceutical agents contain one or more of the compounds according to the invention, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gebiete [Adjuvants for Pharmaceutics and Related Fields]; Pharm. Ind., Issue 2, 1961, page 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G, Aulendorf in Württemberg, 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As a diluent, very frequently oils with or without the addition of a solubilizer, a surfactant, a suspending agent or emulsifier are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, for example, implants can also contain biodegradable polymers or synthetic silicones, such as, for example, silicone rubber. In addition, the active ingredients can be added to, for example, a patch for percutaneous administration. Finally, the compounds can also be administered locally using an intrauterine system (coil, IUD, Mirena$_{(R)}$).

The compounds of general formula I according to the invention are produced as described in the examples. All the compounds of general formula I can be obtained by analogous procedure with use of homologous reagents in the reagents that are described in the examples.

In the process for the production of the compounds of general formula I, a compound of general formula II (II)

in which
R$^1$, R$^2$ and n have the meanings that are already indicated in general Formula I and L stands for a leaving group,
if R$^3$ in the compound of general formula I is to stand for a grouping —(CH$_2$)$_n$NR$^4$R$^5$,
is reacted with a compound of general formula III

H—NR$^4$R$^1$ (III)

in which R$^4$ and R$^5$ have the meaning that is indicated in general formula I, or
if R$^3$ in the compound of general formula I is to stand for a grouping —(CH$_2$)$_n$S(O)$_m$R$^6$—,
is reacted with a compound that provides the thiolate-anion of general formula IV

—SR6 (IV)

in which R$^6$ has the meaning that is indicated in general formula I, and the thio compound that is obtained is then optionally either oxidized to a sulfinyl compound (m=1) or a sulfonyl compound (m=2), or 14,17-ethano-ll-(4-hydroxyphenyl)-17-hydroxyestra-4,9-dien-3-one (V)

(V)

if R$^3$ in the compound of general formula I is to stand for a grouping —(CH$_2$)$_n$OCH$_2$CONR$^4$R$^5$,
is reacted with a compound of general formula VI L—(CH$_2$)$_n$OCH$_2$CONR$^4$R$^5$ (VI)

in which n, R$^4$, R$^5$ have the meaning that is indicated in general formula I and L stands for a leaving group, to a compound of general formula VII

(VII)

and the latter is then converted by aromatization of the A-ring of the steroid skeleton into a compound of general formula I, in which R$^1$ stands for a hydrogen atom and R$^3$ stands for a grouping —(CH$_2$)$_n$OCH$_2$CONR$^4$R$^5$.

In this case, the design of side chain R$^3$ can be carried out quite analogously as already described in U.S. Pat. No. 5,149,696—(R$^3$=—(CH$_2$)$_n$OCH$_2$CONR$^4$R$^5$) and in WO93/13123 (R$^3$=—(CH$_2$)$_n$S(O)$_m$R$^6$).

If R$^3$ is to stand for —(CH$_2$)$_n$NR$^4$R$^5$, the corresponding iodide is reacted with an amine of formula HNR$^4$R$^5$ according to standard processes.

The intermediate compounds of general formula II that have gone through the production of the compounds of general formula I (II)

in which
R¹, R² and n have the meanings that are already indicated in general formula I and L stands for a leaving group also belong to the subject of this invention.

Leaving group L preferably stands for a hydroxy group, a chlorine, bromine or iodine atom or for a tosyl group.

The process according to the invention can also be performed with other leaving groups L that are familiar to one skilled in the art, such as, for example, the mesyl group.

The following intermediate compounds are especially preferred:
- 14,17-Ethano-11β-(4-[5-chloropentyloxy]phenyl)-estra-1,3,5(10)-triene-3,17-diol
- 14,17-ethano-11β-(4-[5-iodopentyloxy]phenyl)-estra-1,3,5(10)-triene-3,17-diol
- 14,17-ethano-11β-(4-[6-hydroxyhexyloxy]phenyl)-estra-1,3,5(10)-triene-3,17-diol
- 3-benzyloxy-14,17-ethano-11B-(4-[6-hydroxyhexyloxy]phenyl)-estra-1,3,5(10)-trien-17-ol
- 3-benzyloxy-14,17-ethano-11β-(4-[6-tosyloxyhexyloxy]phenyl)-estra-1,3,5(10)-trien-17-ol.

Free hydroxy groups R¹ and R² are optionally esterified partially in 3-position or completely in 3- and 17-position with an acid halide or acid anhydride of general formula V (V), in which R¹' means a $C_1$–$C_{12}$ alkanoyl or benzoyl group and X means a chlorine or bromine atom, or partially etherified in 3-position with an alkyl halide of general formula VI (VI), in which R¹'" means a straight-chain or branched-chain $C_1$–$C_{12}$ alkyl group, a $C_3$–$C_7$ cycloalkyl group or a $C_4$–$C_8$ alkylcycloalkyl group and Y means a chlorine, bromine or iodine atom, and optionally esterified in 17-position with an acid halide or acid anhydride of general formula VII (VII), in which R²' means a $C_1$–$C_{12}$ alkanoyl group and X means a chlorine or bromine atom.

EXAMPLES

The following examples are used for a more detailed explanation of the invention:

Example 1

14α,17α-Ethano-11β-{4-[5-pyrrolidin-1-yl)pentyloxy]phenyl}-1,3,5(10)-estratriene-3,17β-diol a) 14,17-Ethano-11β-(4-[dimethyl-tert-butylsilyloxy]phenyl)-17-hydroxyestra-4,9-dien-3-one 34 g of magnesium chips is introduced into 320 ml of tetrahydrofuran and mixed with a solution of 360 g of 4-bromophenol-tert-butyldimethylsilylether in 560 ml of tetrahydrofuran within 1.5 hours. After 0.5 hour at a bath temperature of 80° C., it is cooled to 0° C., mixed with 6 g of copper(I) chloride, stirred for 0.5 hour at 0° C., a solution of 42 g of 3,3-(2,2-dimethyl-trimethylenedioxy)-5α, 10α-epoxy-14,17-ethanoestr-9(11)-en-17-ol [Scholz, S. et al. Liebigs Ann. Chem., (1989), p. 151 (13b)] in 560 ml of tetrahydrofuran is added in drops, and stirring is continued for 0.5 hour at 0° C. Then, a saturated ammonium chloride solution is added, stirred for 0.5 hour at 0° C., diluted with ethyl acetate, washed with sodium chloride solution and evaporated to the dry state in a vacuum.

35 g of crude 11β-(4-[dimethyl-tert-butylsilyloxy]phenyl)-3,3-(2,2-dimethyl-trimethylenedioxy)-14,17-ethanoestr-9-ene-5α,17β-diol is obtained.

The crude 11β-(4-[dimethyl-tert-butylsilyloxy]phenyl)-3,3-(2,2-dimethyltrimethylenedioxy)-14,17-ethanoestr-9-ene-5α,17β-diol is stirred in 180 ml of tetrahydrofuran with 200 ml of glacial acetic acid and 100 ml of water for 3 hours at a bath temperature of 50° C. Then, it is diluted with ethyl acetate, washed four times with sodium bicarbonate and common salt solution, dried on sodium sulfate, evaporated to the dry state in a vacuum and chromatographed on silica gel with hexane/ethyl acetate. 29 g of 14,17-ethano-11β-(4-[dimethyl-tert-butylsilyloxy]phenyl)-17-hydroxyestra-4,9-dien-3-one is obtained as an oil.

b) 14,17-Ethano-11β-(4-hydroxyphenyl)-17-hydroxyestra-4,9-dien-3-one

A solution of 15.1 g of 14,17-ethano-11β-(4-[dimethyl-tert-butylsilyloxy]phenyl)-17-hydroxyestra-4,9-dien-3-one in 65 ml of tetrahydrofuran is stirred with 62 ml of a 1.1 M tetrabutylammonium fluoride solution in tetrahydrofuran for 2 hours at room temperature. Then, ammonium chloride solution is added, poured onto water, extracted three times with ethyl acetate, washed neutral, dried on sodium sulfate and concentrated by evaporation in a vacuum. 13.3 g of crude 14,17-ethano-11β-(4-hydroxyphenyl)-17- hydroxyestra-4,9-dien-3-one is obtained. After chromatography on silica gel with hexane/ethyl acetate, 9.8 g of pure 14,17-ethano-11β-(4-hydroxyphenyl)-17-hydroxyestra-4,9-dien-3-one with a melting point of 285–286° C. is obtained. $[\alpha]^{22}_D$=+67.1° (c=0.515% in chloroform).

c) 14,17-Ethano-11β-(4-[5-chloropentyloxy]phenyl)-17-hydroxyestra-4,9-dien-3-one A solution of 13.3 g of crude in 145 ml of acetone and 40 ml of a 2 M aqueous sodium hydroxide solution is mixed at room temperature with 9.1 ml of 1-bromo-5-chloropentane in 30 ml of acetone and stirred for 3 hours at a bath temperature of 50° C. Then, it is diluted with ethyl acetate, washed with 2 M hydrochloric acid, sodium bicarbonate and sodium chloride solution, dried on sodium sulfate, concentrated by evaporation in a vacuum and chromatographed on silica gel with hexane/ethyl acetate. 8 g of pure 14,17-ethano-11β-(4-[5-chloropentyloxy]phenyl)-17-hydroxyestra-4,9-dien-3-one is obtained as crystals with a melting point of 139° C.

d) 14,17-Ethano-11β-(4-[5-chloropentyloxy]phenyl)-estra-1,3,5(10)-triene-3,17-diol A solution of 8 g of 14,17-ethano-11β-(4-[5-chloropentyloxy]phenyl)-17-hydroxyestra-4,9-dien-3-one in 100 ml of absolute ethanol is stirred with 1 g of palladium on activated carbon for 4.5 hours at a bath temperature of 110° C. Then, it is filtered on Celite, rewashed with ethyl acetate and concentrated by evaporation in a vacuum. 8 g of crude 14,17-ethano-11β-(4-[5-chloropentyloxy]phenyl)-estra-1,3,5(10)-triene-3,17-diol is obtained. If it is chromatographed on silica gel with hexane/ethyl acetate, crystals with a melting point of 215° C. are obtained.

e) 14,17-Ethano-11β-(4-[5-iodopentyloxy]phenyl)-estra-1,3,5(10)-triene-3,17-diol A solution of 8 g of crude 14,17-ethano-11β-(4-[5-chloropentyloxy]phenyl)-estra-1,3,5(10)-triene-3,17-diol in 150 ml of ethylmethylketone is stirred with 6.1 g of sodium iodide for 24 hours at a bath temperature of 80° C. Then, it is diluted with ethyl acetate, washed with water and sodium chloride solution, dried on sodium sulfate, concentrated by evaporation in a vacuum and chromatographed on silica gel with hexane/ethyl acetate. 5.2 g of 14,17-ethano-11β-(4-[5-iodopentyloxy]phenyl)-estra-1,3,5(10)-triene-3,17-diol is obtained.

f) 14α,17α-Ethano-11β-{4-[5-(pyrrolidin-1-yl)pentyloxy]phenyl}-1,3,5(10)-estratriene-3,17β-diol A solution of 500 mg of 14,17-ethano-11β-(4-[5-iodopentyloxy]phenyl)-estra-1,3,5(10)-triene-3,17-diol in 5 ml of dimethylformamide is stirred with 0.3 ml of pyrrolidine for 3.5 hours at a bath temperature of 100° C. For working-up, it is poured on water, extracted with ethyl acetate, washed with 0.1 M hydrochloric acid, washed neutral, dried on sodium sulfate, concentrated by evaporation in a vacuum and chromatographed on silica gel with hexane/ethyl acetate. 110 mg of pure 14α,17α-ethano-11β-{4-[5-(pyrrolidin-1-yl)pentyloxy]phenyl)-1,3,5(10)-estratriene-3,17β-diol is obtained as crystals with a melting point of 208–210° C. $[\alpha]^{22}_D$=−143.5° (c=0.510% in chloroform).

Example 2

14α,17α-Ethano-11β-{4-[5-(pentylthio)pentyloxy]phenyl}-1,3,5(10)-estratriene-3,17β-diol A solution of 292 mg of pentylthioacetate in 2 ml of methanol is added in drops to a solution of 1 g of 14,17-ethano-11β-(4-[5-iodopentyloxy]phenyl)-estra-1,3,5(10)-triene-3,17-diol in 20 ml of dimethylformamide, and it is stirred for 1 hour at room temperature. Then, it is added to 1 M of hydrochloric acid, extracted three times with ethyl acetate, washed neutral, dried on sodium sulfate, concentrated by evaporation in a vacuum and chromatographed on silica gel with hexane/ethyl acetate. 850 mg of pure 14α,17α-ethano-11β-[4-[5-(pentylthio)pentyloxy]phenyl]-1,3,5 (10)-estratriene-3,17β-diol is obtained as crystals with a melting point of 73–75° C. $[\alpha]^{22}_D$=−26.0° (c=0.550% in chloroform)

Example 3

14α,17α-Ethano-11β-{4-[5-(pentanesulfinyl)pentyloxy]-phenyl}-1,3,5(10)-estratriene-3,17β-diol A solution of 400 mg of 14α,17α-ethano-11β-{4-[5-(pentylthio)pentyloxy]phenyl}-1,3,5(10)-estratriene-3,17β-diol in 15 ml of methanol and 0.65 ml of water is stirred with 176 mg of sodium periodate for 4.5 hours at room temperature. For working-up, it is poured on water, extracted three times with ethyl acetate, washed neutral, dried on sodium sulfate, concentrated by evaporation in a vacuum and chromatographed on silica gel with dichloromethane/acetone. 393 mg of pure 14α,17α-ethano-11β-{4-[5-(pentanesulfinyl)pentyloxy]phenyl}-1,3,5(10)-estratriene-3,17β-diol is obtained as crystals with a melting point of 123–128° C. $[\alpha]^{22}_D$=−53.2° (c=0.550% in chloroform)

Example 4

14α,17α-Ethano-11β-{4-[5-(pentanesulfonyl)pentyloxy]phenyl}-1,3,5(10)-estratriene-3,17β-diol A solution of 400 mg of 14α,17α-ethano-11β-{4-[5-(pentylthio)pentyloxy]phenyl}-1,3,5(10)-estratriene-3,17β-diol in 10 ml of 1,2-dichloroethane and 10 ml of tert-butanol is mixed in portions with 507 mg of m-chloroperbenzoic acid, and it is stirred for 2 hours. Then, it is mixed with saturated sodium hydrogen sulfite solution, poured on water, extracted three times with ethyl acetate, washed neutral, dried on sodium sulfate, concentrated by evaporation in a vacuum and chromatographed on silica gel with dichloromethane/acetone. 231 mg of pure 14α,17α-ethano-11β-{4-[5-(pentanesulfonyl)pentyloxy]phenyl}-1,3,5(10)-estratriene-3,17β-diol is obtained as crystals with a melting point of 107–108° C. $[\alpha]^{22}_D$=−38.2° (c=0.5% in chloroform)

Example 5

14α,17α-Ethano-11β-{4-[5-(4,4,5,5,5-pentafluoropentyl-sulfinyl)pentyloxy]phenyl}-1,3,5(10)-estratriene-3,17β-diol a) 14α,17α-Ethano-11β-{4-[5-(4,4,5,5,5-pentafluoropentyl-thio)pentyloxy]phenyl}-1,3,5(10)-estratriene-3,17β-diol A solution of 500 mg of 14,17-ethano-11β-(4-[5-iodopentyloxy]phenyl)-estra-1,3,5(10)-triene-3,17-diol in 10 ml of dimethylformamide is mixed drop by drop at room temperature with a solution of 227.6 mg of 4,4,5,5,5-pentafluoropentyl-1-thioacetate in 1 ml of methanol and 0.19 ml of 30% sodium methylate solution and stirred for 2 hours. Then, it is added to 1 M hydrochloric acid, extracted three times with ethyl acetate, washed neutral, dried on sodium sulfate, concentrated by evaporation in a vacuum and chromatographed on silica gel with hexane/ethyl acetate. 500 mg of 14α,17α-ethano-11β-{4-[5-(4,4,5,5,5-pentafluoropentylthio)pentyloxy]phenyl}-1,3,5(10)-estratriene-3,17β-diol is obtained.

b) 14α,17α-Ethano-11β-{4-[5-(4,4,5,5,5-pentafluoropentylsulfinyl)pentyloxy]phenyl}-1,3,5(10)-estratriene-3,17β-diol A solution of 500 mg of 14α,17α-ethano-11β-{4-[5-(4,4,5,5,5-pentafluoropentyl-thio)pentyloxy]phenyl}-1,3,5(10)-estratriene-3,17β-diol in 15 ml of methanol and 0.65 ml of water is stirred with 200 mg of sodium periodate for 6 hours at room temperature. For working-up, it is poured on water, extracted three times with ethyl acetate, washed neutral, dried on sodium sulfate, concentrated by evaporation in a vacuum and chromatographed on silica gel with dichloromethane/acetone. 390 mg of pure 14α,17α-ethano-11β-{4-[5-(4,4,5,5,5-pentafluoropentylsulfinyl)-pentyloxy]phenyl}-1,3,5(10)-estratriene-3,17β-diol is obtained as crystals with a melting point of 110–115° C. $[\alpha]^{22}_D = -40.3°$ (c=0.505% in chloroform)

Example 6

14α,17α-Ethano-11β-{4-[5-(2-pyridinomethylsulfonyl)-pentyloxy]phenyl}-1,3,5(10)-estratriene-3,17β-diol A solution of 400 mg of 14α,17α-ethano-11β-{4-[5-(2-pyridinomethylsulfinyl)-pentyloxy]phenyl}-1,3,5(10)-estratriene-3,17β-diol (Example 10) in 7.5 ml of 1,2-dichloroethane and 7.5 ml of tert-butanol is mixed in portions with 200 mg of m-chloroperbenzoic acid and stirred for 2 hours. Then, it is mixed with saturated sodium hydrogen sulfite solution, poured on water, extracted three times with ethyl acetate, washed neutral, dried on sodium sulfate, concentrated by evaporation in a vacuum and chromatographed on silica gel with dichloromethane/acetone. 184.4 mg of pure 14α,17α-ethano-11β-{4-[5-(2-pyridinomethylsulfonyl)pentyloxy]phenyl}-1,3,5(10)-estratriene-3,17β-diol is obtained as crystals wtih a melting point of 98–100° C. $[\alpha]^{22}_D = -39.8°$ (c=0.540% in chloroform)

Example 7

14α,17α-Ethano-11β-{4-[6-(4,4,5,5,5-pentafluoropentylthio)hexyloxy]-phenyl}-1,3,5(10)-estratriene-3,17β-diol a) 14,17-Ethano-11β-(4-[6-dimethyl-tert-butylsilyloxyhexyl-oxy]phenyl)-17-hydroxyestra-4,9-dien-3-one A solution of 15 g of 14,17-ethano-11β-(4-hydroxyphenyl)-17-hydroxyestra-4,9-dien-3-one in 150 ml of acetone and 40 ml of 2 M aqueous sodium hydroxide solution is mixed drop by drop at room temperature with a solution of 30 g of 1-bromo-6-dimethyl-tert-butylsilyloxyhexane in 30 ml of acetone, and then it is stirred for 6 hours at 50° C. For working-up, ethyl acetate is added, it is extracted with 2 M hydrochloric acid, washed with sodium bicarbonate and common salt solution, dried on sodium sulfate and concentrated by evaporation in a vacuum. 28.9 g of crude product is obtained. After chromatography on silica gel with hexane/ethyl acetate, 13 g of pure 14,17-ethano-11β-(4-[6-dimethyl-tert-butylsilyloxyhexyloxy]phenyl)-17-hydroxyestra-4,9-dien-3-one is obtained as crystals with a melting point of 122–124° C. $[\alpha]^{12}_D = +121.2°$ (c=0.550% in chloroform)

b) 14,17-Ethano-11β-(4-[6-hydroxyhexyloxy]phenyl)-estra-1,3,5(10)-triene-3,17-diol A solution of 11.1 g of 14,17-ethano-11β-(4-[6-dimethyl-tert-butylsilyloxy-hexyloxy]phenyl)-17-hydroxyestra-4,9-dien-3-one in 111 ml of absolute ethanol is stirred with 1.11 g of palladium on activated carbon for 4 hours at a bath temperature of 100° C. Then, it is filtered on Celite, rewashed with ethyl acetate and concentrated by evaporation in a vacuum. 11 g of crude 14,17-ethano-11β-(4-[6-dimethyl-tert-butylsilyloxy-hexyloxy]phenyl)-estra-1,3,5(10)-triene-3,17-diol is obtained.

A solution of 11 g of crude 14,17-ethano-11β-(4-[6-dimethyl-tert-butylsilyloxy-hexyloxy]phenyl)-estra-1,3,5(10)-triene-3,17-diol in 55 ml of tetrahydrofuran is stirred with 62 ml of glacial acetic acid and 31 ml of water for 2.5 hours at a bath temperature of 50° C. Then, it is diluted with ethyl acetate, washed with sodium bicarbonate and sodium chloride solution, dried on sodium sulfate, concentrated by evaporation in a vacuum and chromatographed on silica gel with dichloromethane/acetone. 8 g of 14,17-ethano-11-(4-[6-hydroxyhexyloxy]phenyl)-estra-1,3,5(10)-triene-3,17-diol is obtained as crystals with a melting point of 116–118° C. $[\alpha]^{22}_D = -18.5°$ (c=0.540% in chloroform)

c) 3-Benzyloxy-14,17-ethano-11β-(4-[6-hydroxyhexyloxy]phenyl)-estra-1,3,5(10)-trien-17-ol A solution of 2.5 g of 14,17-ethano-11β-(4-[6-hydroxyhexyloxy]phenyl)-estra-1,3,5(10)-triene-3,17-diol in 30 ml of acetonitrile is stirred with 774 mg of potassium carbonate and 0.67 ml of benzyl bromide for 3 hours at a bath temperature of 100° C. Then, it is concentrated by evaporation in a vacuum at a bath temperature of 50° C., poured on water, extracted three times with dichloromethane, washed with common salt solution, dried on sodium sulfate, concentrated by evaporation in a vacuum and chromatographed on silica gel with dichloromethane/acetone. 2.1 g of pure 3-benzyloxy-14,17-ethano-11β-(4-[6-hydroxyhexyloxy]phenyl)-estra-1,3,5(10)-trien-17-ol is obtained as crystals with a melting point of 142–144° C. $[\alpha]^{22}_D = -30.1°$ (c=0.520% in chloroform)

d) 3-Benzyloxy-14,17-ethano-11β-(4-[6-tosyloxyhexyloxy]phenyl)-estra-1,3,5(10)-trien-17-ol A solution of 850 mg of 3-benzyloxy-14,17-ethano-11β-(4-[6-hydroxyhexyloxy]phenyl)-estra-1,3,5(10)-trien-17-ol in 10 ml of pyridine is stirred with 500 mg of toluenesulfonic acid anhydride for 3.5 hours at room temperature. For working-up, ethyl acetate is added, extracted with 2 M hydrochloric acid, washed with sodium bicarbonate and common salt solution, dried on sodium sulfate and concentrated by evaporation in a vacuum. 1 g of crude product is obtained. After chromatography on silica gel with hexane/ethyl acetate, 670 mg of pure 3-benzyloxy-14,17-ethano-11β-(4-[6-tosyloxyhexyloxy]phenyl)-estra-1,3,5(10)-trien-17-ol is obtained as crystals with a melting point of 70–71° C. $[\alpha]^{22}_D = -29.3°$ (c=0.525% in chloroform)

e) 3-Benzyloxy-14α,17α-ethano-11β-{4-[6-(4,4,5,5,5-pentafluoropentylthio)hexyloxy]-phenyl}-1,3,5(10)-estratrien-17β-ol A solution of 600 mg of 3-benzyloxy-14,17-ethano-11β-(4-[6-tosyloxyhexyloxy]phenyl)-estra-1,3,5(10)-trien-17-ol in 10 ml of dimethylformamide is mixed drop by drop at room temperature with a solution of 227.6 mg of 4,4,5,5,5-pentafluoropentyl-1-thioacetate in 1 ml of methanol and 0.19 ml of 30% sodium methylate solution, and it is stirred for 2 hours. Then, it is added to 1 M hydrochloric acid, extracted three times with ethyl acetate, washed neutral, dried on sodium sulfate, concentrated by evaporation in a vacuum and chromatographed on silica gel with hexane/ethyl acetate. 630 mg is obtained as an oil. $[\alpha]^{22}_D = -26.4°$ (c=0.525% in chloroform)

f) 14α,17α-Ethano-11β-{4-[6-(4,4,5,5,5-pentafluoropentylthio)hexyloxy]phenyl}-1,3,5(10)-estratriene-3,17β-diol A solution of 600 mg of 3-benzyloxy-14α,17α-ethano-11β-{4-[6-(4,4,5,5,5-penta-fluoropentylthio)hexyloxy]-phenyl}-1,3,5(10)-estratrien-17β-ol in 10 ml of dichloromethane is slowly mixed at 0° C. with 288 mg of N,N-dimethylaniline, and after 420 mg of aluminum trichloride is added, it is stirred for 4 hours at 0° C. Then, it is mixed at 0° C. with water, acidified with 1 M sulfuric acid, extracted three times with ethyl acetate, washed neutral, dried on sodium sulfate, concentrated by evaporation in a vacuum and chromatographed on silica gel with hexane/ethyl acetate. 430.3 mg of 14α,17α-ethano-11β-{4-[6-(4,4,5,5,5-pentafluoropentylthio)hexyloxy]-phenyl}-1,3,5(10)-estratriene-3,17β-diol is obtained as crystals of 63–64° C. $[\alpha]^{22}_D = -32.6°$ (c=0.515% in chloroform)

Example 8

14α,17α-Ethano-11β-{4-[6-(4,4,5,5,5-pentafluoropentyl)-sulfinyl]hexyloxy}phenyl-1,3,5(10)-estratriene-3,17β-diol A solution of 180 mg of 14α,17α-ethano-11β-{4-[6-(4,4,5,5,5-pentafluoropentyl-thio)hexyloxy]-phenyl}-1,3,5(10)-estratriene-3,17β-diol in 5.4 ml of methanol and 0.23 ml of water is stirred with 72 mg of sodium periodate for 5 hours at room temperature. For working-up, it is poured on water, extracted three times with ethyl acetate, washed neutral, dried on sodium sulfate, concentrated by evaporation in a vacuum and chromatographed on silica gel with dichloromethane/acetone. 134 mg of pure 14α,17α-ethano-11β-{4-[6-(4,4,5,5,5-pentafluoropentyl)sulfinyl]hexyloxy}phenyl-1,3,5(10)-estratriene-3,17β-diol is obtained as crystals with a melting point of 118–120° C. $[\alpha]^{22}_D = -38.3°$ (c=0.530% in chloroform)

Example 9

14α,17α-Ethano-11β-{4-[6-(4,4,5,5,5-pentafluoropentyl)-sulfonyl]hexyloxy}-phenyl-1,3,5(10)-estratriene-3,17β-diol A solution of 200 mg of 14α,17α-ethano-11β-{4-[6-(4,4,5,5,5-pentafluoropentyl-thio)hexyloxy]-phenyl}-1,3,5(10)-estratriene-3,17β-diol in 3.5 ml of 1,2-dichloroethane and 3.5 ml of tert-butanol is mixed in portions with 100 mg of m-chloroperbenzoic acid and stirred for 1 hour. Then, it is added to saturated sodium hydrogen sulfite solution, extracted three times with ethyl acetate, washed neutral, dried on sodium sulfate, concentrated by evaporation in a vacuum and chromatographed on silica gel with hexane/ethyl acetate. 154 mg of pure 14α,17α-ethano-11β-{4-[6-(4,4,5,5,5-pentafluoropentyl)sulfonyl]hexyloxy}-phenyl-1,3,5(10)-estratriene-3,17β-diol is obtained as crystals with a melting point of 93–95° C. $[\alpha]^{22}_D = -38.0°$ (c=0.515% in chloroform)

Example 10

14α,17α-Ethano-11β-{4-[5-(2-pyridinomethylsulfinyl)-pentyloxy]phenyl}-1,3,5(10)-estratriene-3,17-diol a) 14α,17α-Ethano-11β-{4-[5-(2-pyridinomethylthio)-pentyloxy]phenyl}-1,3,5(10)-estratriene-3,17β-diol A solution of 1.94 g of 14,17-ethano-11β-(4-[5-iodopentyloxy]phenyl)-estra-1,3,5(10)-triene-3,17-diol in 40 ml of methanol is added in drops to a prepared solution of 12.5 g of a 10% ethanolic 2-mercaptomethylpyridine solution and 1.7 ml of 30% sodium methylate solution, mixed with 600 mg of sodium iodide and stirred for 1 hour at a bath temperature of 80° C. For working-up, it is poured on water, extracted three times with ethyl acetate, washed with saturated common salt solution, dried on sodium sulfate, concentrated by evaporation in a vacuum and chromatographed on silica gel with dichloromethane/acetone. 14α,17α-Ethano-11β-{4-[5-(2-pyridinomethylthio)pentyloxy]phenyl}-1,3,5(10)-estratriene-3, 17β-diol is obtained as crystals with a melting point of 93–95° C. $[\alpha]^{22}_D = -44.1°$ (c=0.525% in chloroform)

b) 14α,17α-Ethano-11β-{4-[5-(2-pyridinomethylsulfinyl)-pentyloxy]phenyl}-1,3,5(10)-estratriene-3,17β-diol A solution of 1.3 g of 14α,17α-ethano-11β-{4-[5-(2-pyridinomethylthio)pentyloxy]phenyl}-1,3,5(10)-estratriene-3,17β-diol in 50 ml of methanol and 2.1 ml of water is stirred with 570 mg of sodium periodate for 3.5 hours at room temperature. For working-up, it is poured on water, extracted three times with ethyl acetate, washed neutral, dried on sodium sulfate, concentrated by evaporation in a vacuum and chromatographed on silica gel with dichloromethane/acetone. 1.1 g of pure 14α,17α-ethano-11-{4-[5-(2-pyridinomethylsulfinyl)pentyloxy]phenyl}-1,3,5(10)-estratriene-3,17β-diol is obtained as crystals with a melting point of 118–120° C. $[\alpha]^{22}_D = -52.6°$ (c=0.505% in chloroform)

Example 11

14α,17α-Ethano-11β-{4-[5-(4,4,5,5,5-pentafluoropentyl)-sulfonyl]pentyloxy}phenyl-1,3,5(10)-estratriene-3,17β-diol A solution of 1.85 g of 14α,17α-ethano-11β-{4-[5-(4,4,5,5,5-pentafluoropentyl-thio)pentyloxy]phenyl}-1,3,5(10)-estratriene-3,17β-diol in 72 ml of 1,2-dichloroethane and 72 ml of tert-butanol is mixed in portions with 2.6 g of m-chloroperbenzoic acid and stirred for 1 hour at room temperature. Then, it is diluted wtih dichloromethane, washed with saturated sodium hydrogen sulfite, sodium bicarbonate and common salt solution, dried on sodium sulfate, concentrated by evaporation in a vacuum and chromatographed on silica gel with hexane/ethyl acetate. 800 mg of pure 14α,17α-ethano-11β-{4-[5-(4,4,5,5,5-pentafluoropentyl)sulfonyl]pentyloxy}phenyl-1,3,5(10)-estratriene-3,17β-diol is obtained. $[\alpha]^{22}_D = -36.6°$ (c=0.5% in chloroform)

Example 12

2-(6-[4-{14,17-Ethano-3,17-dihydroxyestra-1,3,5(10)-trien-11β-yl}-phenoxy]-hexyloxy)acetic acid-(N-butyl-N-methyl)-amide a) 2-(6-[4-{14,17-Ethano-17-hydroxyestra-3-oxo-4,9-dien-11β-yl}phenoxy]hexyloxy)acetic acid-(N-butyl-N-methyl)-amide A solution of 2.5 g of 14,17-ethano-11β-(4-hydroxyphenyl)-17-hydroxyestra-4,9-dien-3-one in 40 ml of methanol and 10 ml of 2 M aqueous sodium hydroxide solution is mixed drop by drop with 3.8 g of 2-(6-bromohexyloxy)acetic acid-(N-butyl-N-methyl)-amide in 6 ml of acetone and stirred for 4.5 hours at a bath temperature of 50° C. Then, it is diluted with ethyl acetate, washed with 1 M hydrochloric acid, washed with sodium bicarbonate and common salt solution, dried on sodium sulfate, concentrated by evaporation in a vacuum and chromatographed on silica gel with hexane/ethyl acetate. 3.1 g of pure 2-(6-[4-{14,17-ethano-17-hydroxyestra-3-oxo-4,9-dien-11β-yl}phenoxy]hexyloxy)acetic acid-(N-butyl-N-methyl)-amide is obtained as a foam. $[\alpha]^{22}_D = +126.6°$ (c=0.525% in chloroform)

b) 2-(6-[4-{14,17-Ethano-3,17-dihydroxyestra-1,3,5(10)-trien-11β-yl}-phenoxy]-hexyloxy)acetic acid-(N-butyl-N-methyl)-amide A solution of 500 mg of 2-(6-[4-{14,17-ethano-17-hydroxyestra-3-oxo-4,9-dien-11β-yl}phenoxy]hexyloxy)acetic acid-(N-butyl-N-methyl)-amide in 10 ml of methanol is stirred with 0.5 g of palladium hydroxide on magnesium oxide for 0.5 hour at a bath temperature of 80° C. Then, it is filtered on Celite, rewashed with ethyl acetate, concentrated by evaporation in a vacuum and chromatographed on silica gel with hexane/ethyl acetate. 130 mg of pure 2-(6-[4-{14,17-ethano-3,17-dihydroxyestra-1,3,5(10)-trien-11β-yl}-phenoxy]-hexyloxy)acetic acid-(N-butyl-N-methyl)-amide is obtained as crystals with a melting point of 94–95° C. $[\alpha]^{22}_D = -32.2°$ (c=0.500% in chloroform)

TABLE 1

Antiestrogenic/Estrogenic Action In Vitro

| | Antagonism | | Agonism |
|---|---|---|---|
| | HELA | MVLN | HELA (rPR-TK) |
| Compound | $IC_{50}$ [nM] | | [% of estradiol] |
| A | 0.4 | — | 16 |
| B | 0.3 | 0.4 | 50 |
| V | 0.14 | 1.0 | 37 |

TABLE 2

Uterus Growth Test

| Compound | Type of Administration | Uterus Weight % E2 | Epithelial Height % E2 |
|---|---|---|---|
| 0.01 mg/kg of A | s.c. | 2 | 6 |
| 0.1 mg/kg of A | s.c. | 0 | -16 |
| 1 mg/kg of A | s.c. | -7 | -8 |
| 10 mg/kg of A | s.c. | -15 | -22 |
| 0.01 mg/kg of B | s.c. | 3 | 4 |
| 0.1 mg/kg of B | s.c. | 31 | 19 |
| 1 mg/kg of B | s.c. | 14 | 18 |
| 10 mg/kg of B | s.c. | 6 | 13 |
| 0.03 mg/kg of V | s.c. | 28 | 18 |
| 0.3 mg/kg of V | s.c. | 32 | 33 |
| 3 mg/kg of V | s.c. | 19 | 27 |

TABLE 3

Antiuterus Growth Test

| Compound | Type of Administration | Uterus Weight % of Inhibition |
|---|---|---|
| 0.1 mg/kg of A | s.c. | 33 |
| 1 mg/kg of A | s.c. | 88 |
| 10 mg/kg of A | s.c. | 121 |
| 0.1 mg/kg of B | s.c. | 32 |
| 1 mg/kg of B | s.c. | 83 |
| 10 mg/kg of B | s.c. | 100 |
| 0.3 mg/kg of V | s.c. | 57 |

TABLE 4

Bone Density Findings
Compound A

| Group | Test Substance | Dose/ Animal s.c. | Bone Density Femur mg Ca/ccm | % of Action of E2 | TB/TV (Tibia) in % | % of Action of E2 |
|---|---|---|---|---|---|---|
| 1 | ovx-control | — | 286.1 | | 16.1 | |
| 2 | 17β-estradiol | 0.3 µg | 361.7 | 100 | 34.0 | |
| 3 | Compound A | 0.1 µg | 296.4 | 14 | 17.2 | 4.1 |
| 4 | Compound A | 1 µg | 309.6 | 31 | 18.9 | 17 |
| 5 | Compound A | 10 µg | 331.3 | 60 | 22.5 | 35 |
| 6 | Compound A | 100 µg | 324.1 | 50 | 27.0 | 62 |
| 7 | sham | — | | | 32.2 | |

TABLE 5

Compound A

| Group | Test Substance | Dose/ Animal s.c. | Bone Density-mg Ca/ccm | % of Action of E2 |
|---|---|---|---|---|
| 1 | ovx-control | — | 299.4 | |
| 2 | 17β-estradiol | 0.3 µg | 375.2 | 100 |
| 3 | compound A | 100 µg | 361.8 | 82 |
| 4 | compound A | 500 µg | 336.3 | 49 |
| 5 | compound A | 2000 µg | 348.8 | 65 |

TABLE 6

Compound B

| Group | Test Substance | Dose/ Animal s.c. | TB/TV (Tibia) in % | % of Action of E2 |
|---|---|---|---|---|
| 1 | ovx-control | — | 13.0 | |
| 2 | 17β-estradiol | 0.3 µg | 26.0 | 100 |
| 3 | compound B | 1 µg | 19.6 | 52 |
| 4 | compound B | 10 µg | 18.9 | 47 |
| 5 | compound B | 100 µg | 18.6 | 45 |

TABLE 7

Compound V

| Group | Test Substance | Dose/ Animal s.c. | Bone Density Tibia - mg Ca/ccm | % of Action of E2 |
|---|---|---|---|---|
| 1 | ovx-control | — | 293.7 | |
| 2 | 17β-estradiol | 0.3 µg | 402.9 | 100 |
| 3 | compound V | 10 µg | 337.3 | 40 |
| 4 | compound V | 100 µg | 331.2 | 34.4 |
| 5 | compound V | 250 µg | 374.3 | 74 |

What is claimed is:
1. An 11β-aryl-substituted 14,17-ethanoestratriene compound of formula I

(I)

in which
R$^1$ stands for a hydrogen atom, a C$_1$–C$_{12}$ alkanoyl group, a benzoyl group, a straight-chain or branched-chain C$_1$–C$_{12}$ alkyl group, a C$_3$–C$_7$ cycloalkyl group or a C$_4$–C$_8$ alkylcycloalkyl group, which all can optionally be substituted, R$^2$ stands for a hydrogen atom or an optionally substituted C$_1$–C$_{12}$ alkanoyl group and R$^3$ stands for a grouping —(CH$_2$)$_n$NR$^4$R$^5$ or —(CH$_2$)$_n$OCH$_2$CONR$^4$R$^5$ or —(CH$_2$)$_n$S(O)$_m$R$^6$, in which
n is 4, 5, 6 or 7,
m is 0, 1 or 2, R$^4$ or R$^5$, independently of one another, mean a hydrogen atom or a straight-chain or branched, optionally substituted C$_1$–C$_8$ alkyl group, which can also be partially or completely fluorinated, or R$^4$ and R$^5$ together mean a methylene to pentamethylene group —(CH$_2$)$_p$—(p=1–5), and R$^6$ has the meaning of R$^4$ or R$^5$ or is an optionally substituted aryl or arylalkyl radical, whereby the alkyl radical can have up to 6 carbon atoms in it and the aryl radical alone or in the arylalkyl radical is a 5- or 6-membered monocyclic ring or a condensed, 8- to 10-membered ring system, and the aryl radical can have one or more heteroatoms that are selected from among oxygen, nitrogen and sulfur.

2. An 11β-aryl-substituted 14,17-ethanoestratriene compound according to claim 1, in which R$^1$ is a hydrogen atom.

3. An 11β-aryl-substituted 14,17-ethanoestratriene compound according to claim 1, in which R$^2$ is a hydrogen atom.

4. An 11β-aryl-substituted 14,17-ethanoestratriene compound according to claim 1, in which R$^3$ stands for a grouping —(CH$_2$)$_n$NR$^4$R$^5$.

5. An 11β-aryl-substituted 14,17-ethanoestratriene compound according to claim 1, in which R$^3$ stands for a grouping —(CH$_2$)$_n$OCH$_2$CONR$^4$R$^5$.

6. An 11β-aryl-substituted 14,17-ethanoestratriene compound according to claim 1, in which R$^3$ stands for a grouping —(CH$_2$)$_n$S(O)$_m$R$^6$.

7. An 11β-aryl-substituted 14,17-ethanoestratriene compound according to claim 6, in which R$^6$ stands for an n-pentyl group or —CH$_2$-(2-pyridine) group, —CH$_2$-(3-pyridine) group or —CH$_2$-(4-pyridine) group.

8. An 11β-aryl-substituted 14,17-ethanoestratriene compound according to claim 6, in which R$^6$ stands for a 4,4,5,5,5-pentafluoropentyl group.

9. An 11α-aryl-substituted 14,17-ethanoestratriene compound according to claim 1, in which R$^3$ stands for one of the following substituents:

—(CH$_2$)$_5$S(CH$_2$)$_4$CH$_3$;
—(CH$_2$)$_5$SO(CH$_2$)$_4$CH$_3$;
—(CH$_2$)$_5$SO$_2$(CH$_2$)$_4$CH$_3$;
—(CH$_2$)$_5$SO(CH$_2$)$_3$CF$_2$CF$_3$;
—(CH$_2$)$_5$SO$_2$—CH$_2$-(2-pyridyl);
—(CH$_2$)$_5$SO$_2$—CH$_2$-(3-pyridyl);
—(CH$_2$)$_5$SO$_2$—CH$_2$-(4-pyridyl);
—(CH$_2$)$_6$—O—CH$_2$C(O)N(CH$_3$)C$_4$H$_9$;
—(CH$_2$)$_5$—SO$_2$(CH$_2$)$_3$CF$_2$CF$_3$;
—(CH$_2$)$_5$SO—CH$_2$-(2-pyridyl);
—(CH$_2$)$_5$SO—CH$_2$-(3-pyridyl);
—(CH$_2$)$_5$SO—CH$_2$-(4-pyridyl);
—(CH$_2$)$_5$-pyrrolidinyl;
—(CH$_2$)$_6$S(CH$_2$)$_3$CF$_2$CF$_3$;
—(CH$_2$)$_6$SO(CH$_2$)$_3$CF$_2$CF$_3$; or
—(CH$_2$)$_6$SO$_2$(CH$_2$)$_3$CF$_2$CF$_3$.

10. A compound according to claim 1, which is:

14α,17α-ethano-11β-{4-[5-(pyrrolidin-1-yl)pentyloxy]phenyl}-1,3,5(10)-estratriene-3,17β-diol;

14α,17α-ethano-11β-{4-[5-(pentylthio)pentyloxy]phenyl}-1,3,5(10)-estratriene-3,17β-diol;

14α,17α-ethano-11β-{4-[5-(pentanesulfinyl)pentyloxy]phenyl}-1,3,5(10)-estratriene-3,17β-diol;

14α,17α-ethano-11β-{4-[5-(petanesulfonyl)pentyloxy]phenyl}-1,3,5(10)-estratriene-3,17β-diol;

14α,17α-ethano-11β-{4-[5-(4,4,5,5,5-pentafluoropentylsulfinyl)pentyloxy]phenyl}-1,3,5(10)-estratriene-3,17β-diol;

14α,17α-ethano-11β-{4-[5-(2-pyridinomethylsulfonyl)pentyloxy]phenyl}-1,3,5(10)-estratriene-3,17β-diol;

14α,17α-ethano-11β-{4-[6-(4,4,5,5,5-pentafluoropentylthio)hexyloxy]-phenyl}-1,3,5(10)-estratriene-3,17β-diol;

14α,17α-ethano-11β-{4-[6-(4,4,5,5,5-pentafluoropentyl)sulfinyl]hexyloxy}phenyl-1,3,5(10)-estratriene-3,17β-diol;

14α,17α-ethano-11β-{4-[6-(4,4,5,5,5-pentafluoropentyl)sulfonyl]hexyloxy}phenyl-1,3,5(10)-estratriene-3,17β-diol;

14α,17α-ethano-11β-{4-[5-(2-pyridinomethylsulfinyl)pentyloxy]phenyl}-1,3,5(10)-estratriene-3,17β-diol;

14α,17α-ethano-11β-{4-[5-(4,4,5,5,5-pentafluoropentyl)sulfonyl]pentyloxy}phenyl-1,3,5(10)-estratriene-3,17β-diol; or

2-(6-(4-[10-{14,17-ethano-3,17-dihydroxyestra-1,3,5(10)-trien-11β-yl}]-phenoxy)hexyloxy)acetic acid-(N-butyl-N-methyl)-amide.

11. A pharmaceutical composition that contains at least one compound of formula I according to claim 1 as well as a pharmaceutically compatible vehicle.

12. A pharmaceutical composition according to claim 11, which comprises the compound of the formula I in a dose of 0.8 to 800 mg.

13. A process for the production of a compound of formula I of claim 1, which comprises:

if R$^3$ in the compound of general formula I is to stand for a grouping —(CH$_2$)$_n$NR$^4$R$^5$, reacting a compound of formula II (II)

in which
R¹, R² and n have the meanings that are already indicated in formula I and L stands for a leaving group,
with a compound of formula III

H—NR⁴R⁵ (III)

in which R⁴ and R⁵ have the meaning that is indicated in formula I; or if R³ in the compound of formula I is a grouping —$(CH_2)_nS(O)_mR^6$, reacting a compound of the formula II with a compound that provides the thiolate-anion of formula IV (IV)

in which R⁶ has the meaning that is indicated in formula I, and the thio compound that is obtained is then optionally either oxidized to a sulfinyl compound (m=1) or sulfonyl compound (m=2); or if R³ in the compound of general formula I is a grouping —$(CH_2)_nOCH_2CONR^4R^5$, reacting

14,17-ethano-11β-(4-hydroxyphenyl)-17-hydroxyestra-4,9-dien-3-one (V)

(V)

with a compound of formula VI

(VI)

in which n, R⁴, R⁵ have the meaning that is indicated in formula I and L stands for a leaving group, to obtain a compound of general formula VII (VII)

and converting the latter by aromatization of the A-ring of the steroid skeleton into a compound of formula I, in which R¹ stands for a hydrogen atom and R³ stands for a grouping —$(CH_2)_nOCH_2CONR^4R^5$.

14. An intermediate compound of formula II (II)

in which
R¹ stands for a hydrogen atom, a $C_1$–$C_{12}$ alkanoyl group, a benzoyl group, a straight-chain or branched-chain $C_1$–$C_{12}$ alkyl group, a $C_3$–$C_7$ cycloalkyl group or a $C_4$–$C_8$ alkylcycloalkyl group, which all can optionally be substituted,
R² stands for a hydrogen atom or an optionally substituted $C_1$–$C_{12}$ alkanoyl group,
n is 4, 5, 6 or 7, and
L stands for a leaving group.

15. An intermediate compound of formula II according to claim 14, in which R¹ and R² each stand for a hydrogen atom, n stands for 5 or 6 and L stands for a hydroxy group, a chlorine, bromine or iodine atom or for a tosyl group.

16. An intermediate compound of formula II according to claim 14, which is:

14,17-ethano-11β-(4-[5-chloropentyloxy]phenyl)-estra-1,3,5(10)-triene-3,17-diol;

14,17-ethano-11β-(4-[5-iodopentyloxy]phenyl)-estra-1,3,5(10)-triene-3,17-diol;

14,17-ethano-11β-(4-[6-hydroxyhexyloxy]phenyl)-estra-1,3,5(10)-triene-3,17-diol;

3-benzyloxy-14,17-ethano-11β-(4-[6-hydroxyhexyloxy]phenyl)-estra-1,3,5(10)-trien-17-ol; or 3-benzyloxy-14,17-ethano-11β-(4-[6-tosyloxyhexyloxy]phenyl)-estra-1,3,5(10)-trien-17-ol.

* * * * *